US 6,682,477 B2

(12) United States Patent
Boebel et al.

(10) Patent No.: US 6,682,477 B2
(45) Date of Patent: Jan. 27, 2004

(54) HYSTEROSCOPE

(75) Inventors: Manfred Boebel, Bauschlott (DE); Sybille Brüstle, Sternenfels (DE); Dieter Metsch, Kraichtal-Bahnbrücken (DE); Adolf Gallinat, Helmstorf/Seevetal (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 09/793,007

(22) Filed: Feb. 26, 2001

(65) Prior Publication Data

US 2001/0018550 A1 Aug. 30, 2001

(30) Foreign Application Priority Data

Feb. 25, 2000 (DE) .......................... 100 09 020

(51) Int. Cl.⁷ ............................. A61B 1/12; A61B 8/12
(52) U.S. Cl. .................. 600/107; 600/156; 600/121; 600/104; 600/153
(58) Field of Search ................ 600/107, 125, 600/133, 152, 153, 154, 156, 159, 104, 101, 106; 606/108, 119

(56) References Cited

U.S. PATENT DOCUMENTS

| | | | |
|---|---|---|---|
| 2,129,391 A | | 9/1938 | Wappler |
| 4,436,087 A | | 3/1984 | Ouchi ............... 128/6 |
| 4,452,236 A | * | 6/1984 | Utsugi ............. 600/107 |
| 4,641,634 A | * | 2/1987 | Storz ............... 600/104 |
| 4,841,949 A | | 6/1989 | Shimizu et al. ........ 128/4 |
| 5,287,845 A | | 2/1994 | Faul et al. ............ 128/7 |
| 5,320,091 A | | 6/1994 | Grossi et al. .......... 128/7 |
| 5,343,853 A | | 9/1994 | Komi ................ 128/4 |
| 5,456,673 A | * | 10/1995 | Ziegler et al. ....... 600/104 |
| 5,509,892 A | * | 4/1996 | Bonnet ............. 600/129 |
| 5,947,994 A | | 9/1999 | Louw et al. |
| 6,152,870 A | * | 11/2000 | Diener ............. 600/104 |
| 6,282,442 B1 | * | 8/2001 | DeStefano et al. ..... 600/121 |
| 6,299,576 B1 | * | 10/2001 | Ouchi ............. 600/104 |
| 6,358,200 B1 | * | 3/2002 | Grossi ............. 600/121 |
| 6,390,973 B1 | * | 5/2002 | Ouchi ............. 600/104 |

OTHER PUBLICATIONS

Company catalogue of Karl Storz GmbH, Issue 6–94, p. HYST–18.

* cited by examiner

*Primary Examiner*—Henry Bennett
*Assistant Examiner*—Kathryn Ferko
(74) *Attorney, Agent, or Firm*—Cohen, Pontani, Lieberman & Pavane

(57) ABSTRACT

A hysteroscope for carrying out endoscopic operations in the uterus by way of an auxiliary instrument, consists of an inner shank and an outer shank surrounding the inner shank whilst forming a longitudinal channel, of a first fitting for supplying rinsing fluid to be supplied through the inner shank into the uterus and of a second fitting for removing rinsing fluid from the uterus via the longitudinal channel. Furthermore there are provided a third fitting on which the auxiliary instrument is introducable into the hysteroscope and is further distally movable through a working channel, and deflection means with which the distal end region of the auxiliary instrument is elastically laterally deflectable. In the distal end region of the hysteroscope there is provided a first ramp on which, sliding up, the distal end of the auxiliary instrument moved distally through the hysteroscope is deflectable, in order with a further distal movement of the auxiliary instrument to bring its distal end region into a first position. With the help of a pivotable deflection element the distal end region of the auxiliary instrument is deflected into a second position beyond the first position.

15 Claims, 9 Drawing Sheets

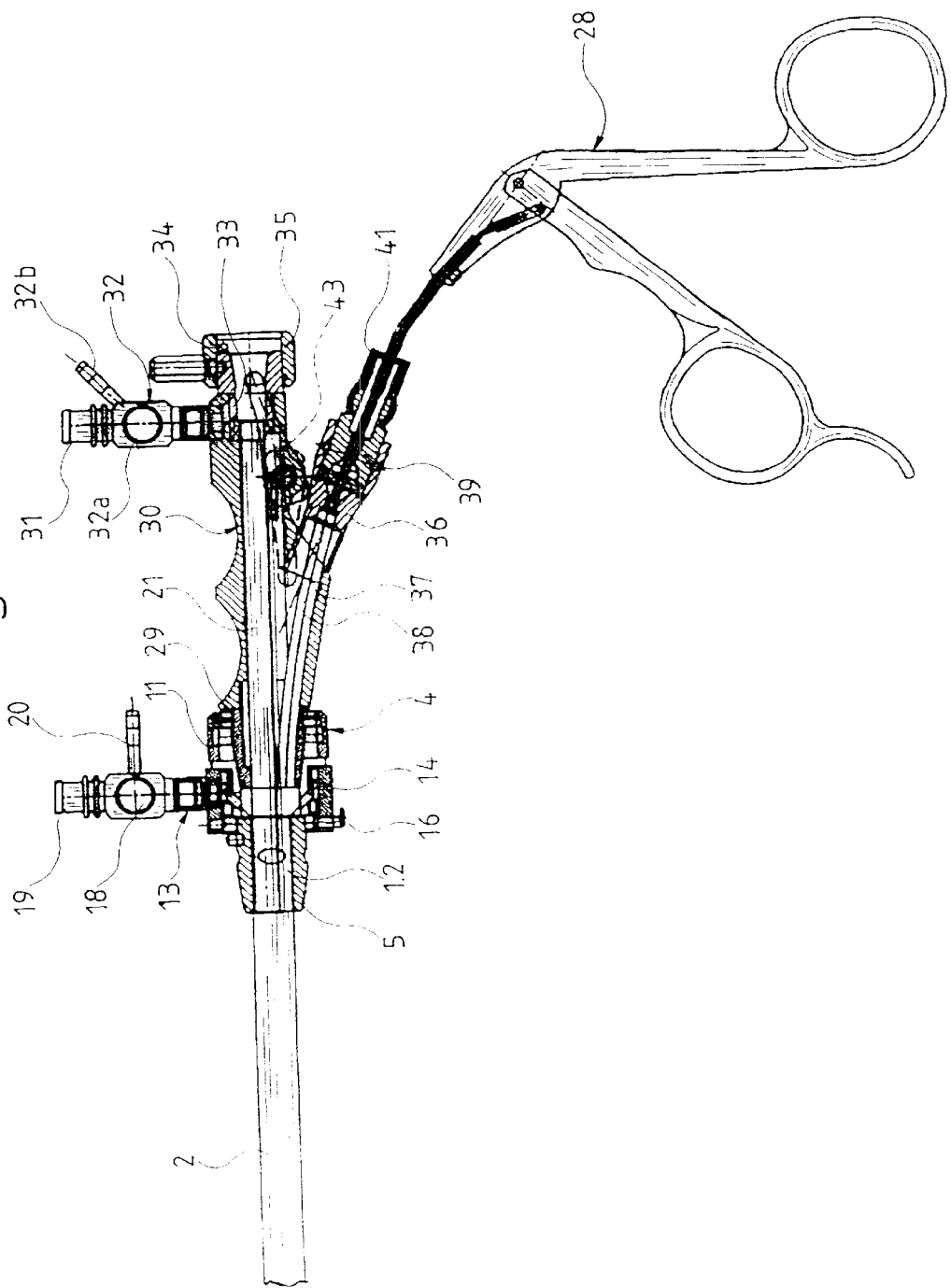

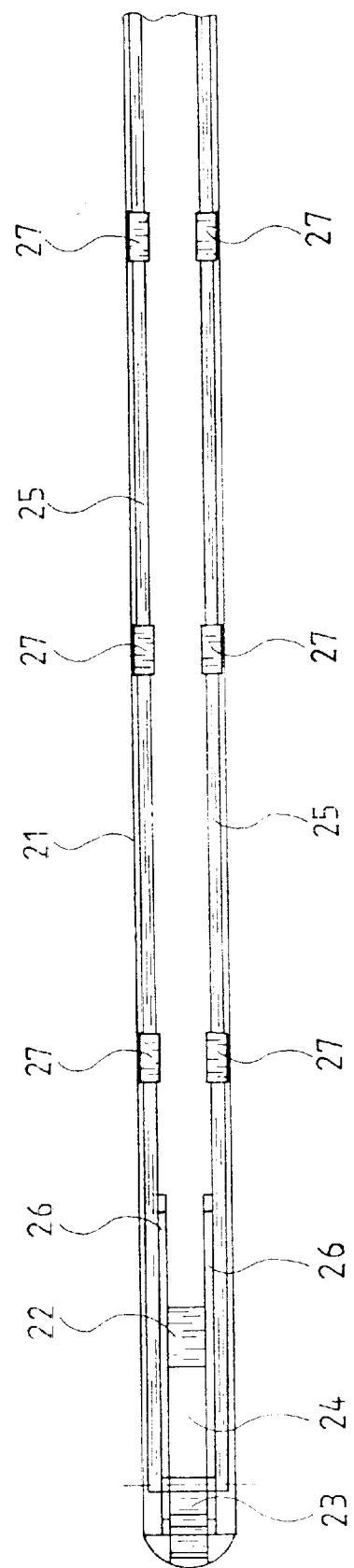

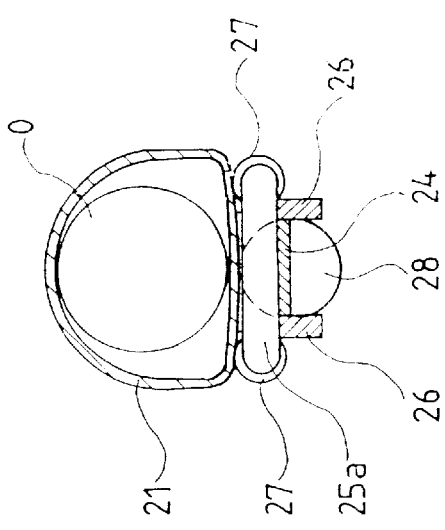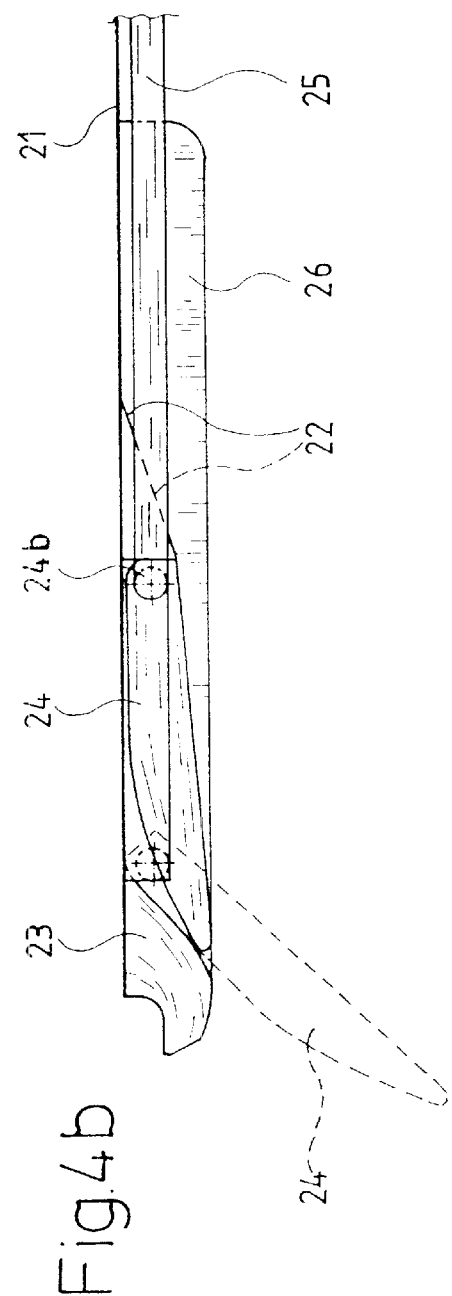

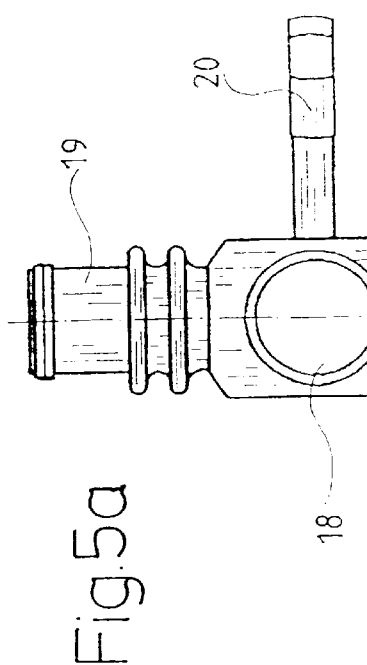
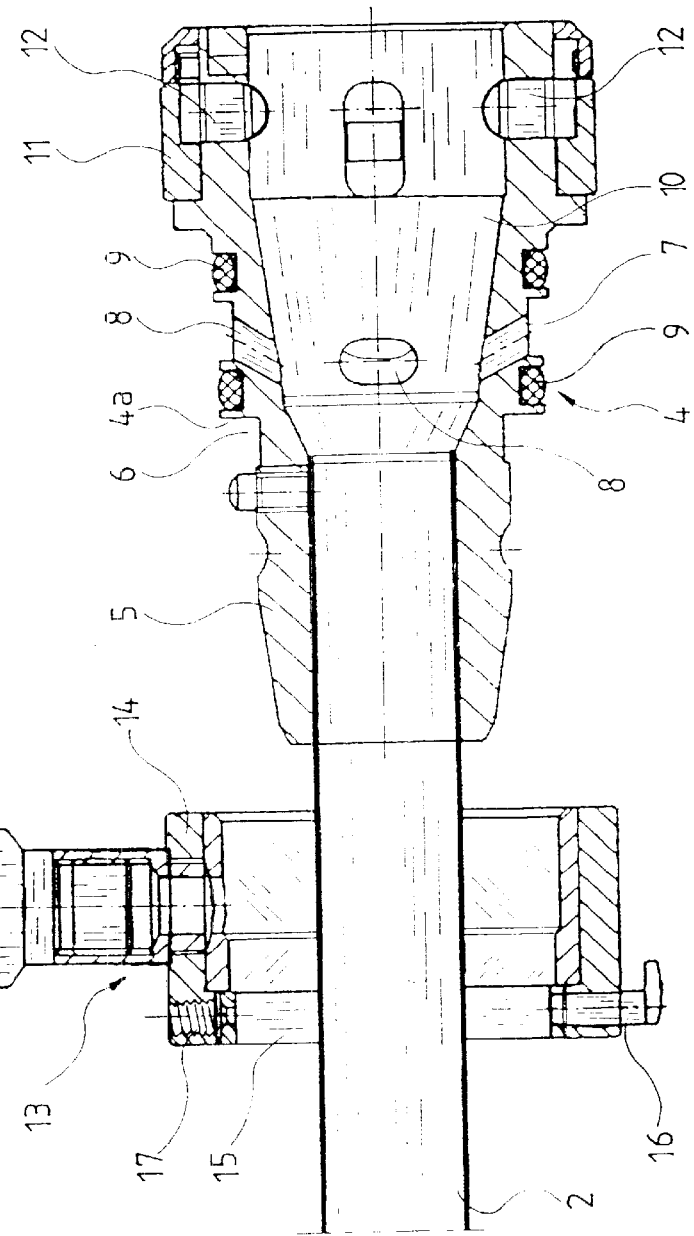
Fig.5a
Fig.5b

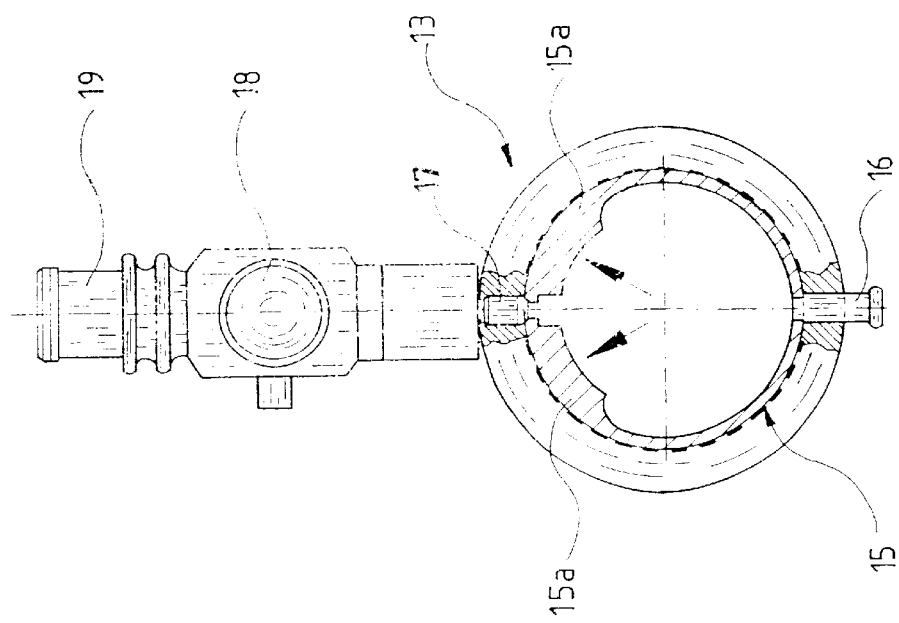

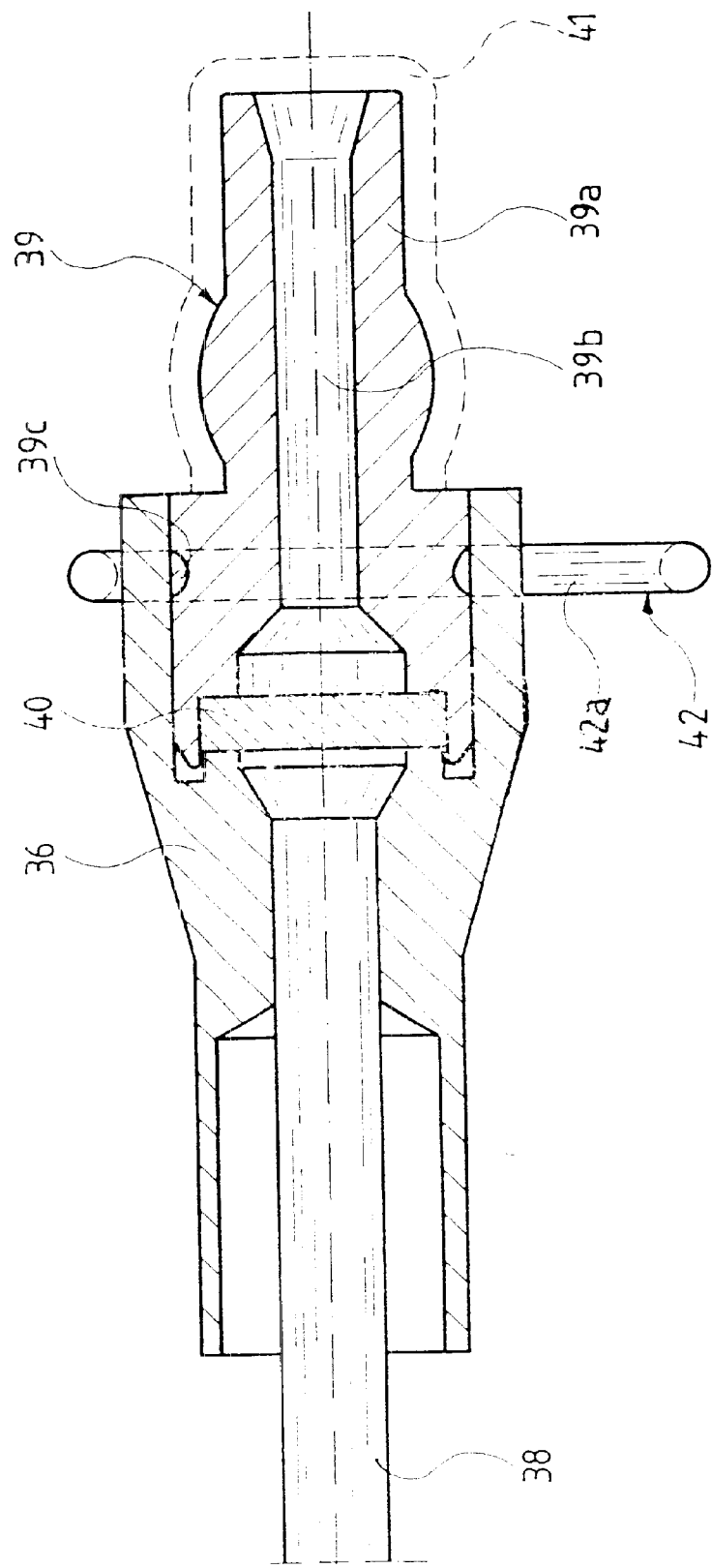

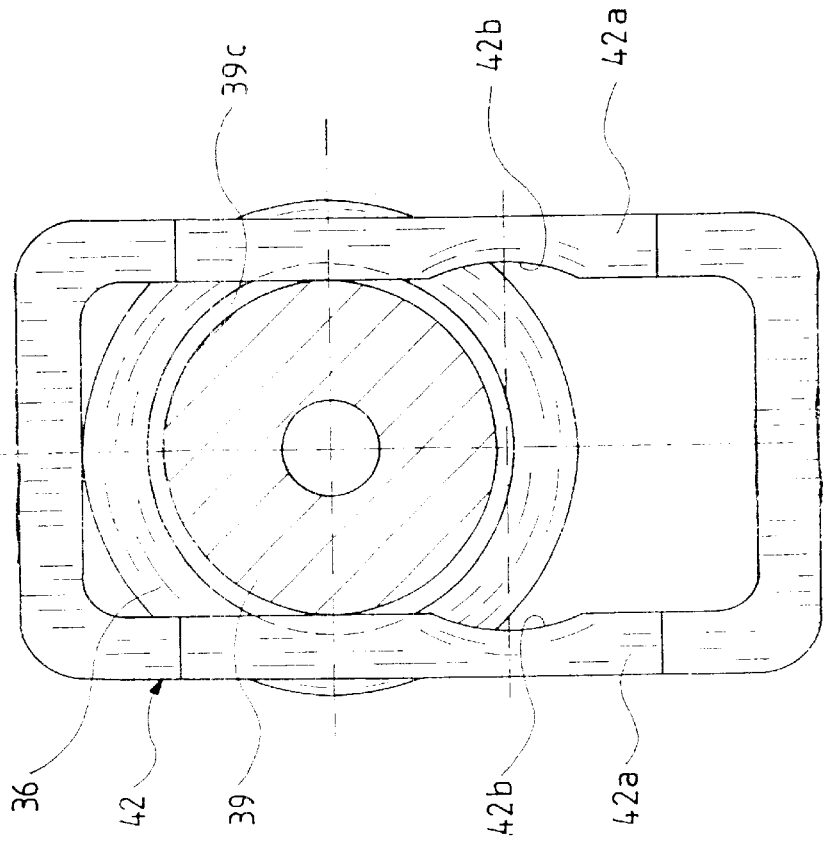

HYSTEROSCOPE

BACKGROUND OF THE INVENTION

1. Field of the Invention

The invention relates to a hysteroscope for carrying out endoscopic operations in the uterus by way of an auxiliary instrument. The hysteroscope includes an inner shank and an outer shank surrounding the inner shank whilst forming a longitudinal channel, a first fitting for supplying rinsing fluid to be led through the inner shank into the uterus, a second fitting for removing rinsing fluid from the uterus via the longitudinal channel, a third fitting at which the auxiliary instrument is introducable into the hysteroscope and is further distally movable through a working channel, and of deflection means with which the distal end region of the auxiliary instrument is elastically laterally deflectable.

2. Description of the Related Art

With such operation hysteroscopes e.g. with the help of forceps and laser probes as auxiliary instruments, myonlas on or in the uterus wall are removed, and specifically with the simultaneous rinsing of the body cavity in order to ensure a good viewing of the operational region by way of optics running through the endoscope. There is also required a lateral deflection of the distal end of the end section of the auxiliary instrument, which projects out of the endoscope, in order to be able lead the end of the auxiliary instrument freely and unhindered to the operation location.

The deflection with the use of flexible auxiliary instruments is not problematic and may be carried out with a pivotable lever located distally on the endoscope, also called an Albarran lever. A lateral deflection of the distal auxiliary instrument by way of a ramp is also possible (U.S. Pat. No. 2,129,391 and U.S. Pat. No. 5,947,994).

This however does not function with semi-rigid or relatively rigid auxiliary instruments since for their deflection relatively large bending forces are required which may not be mustered by a pivotable lever or deflection element without supporting measures. Although an elastic deflection of relatively rigid end sections of auxiliary instruments via the oblique surface of a ramp is possible, the ramp however may not be too steep since otherwise the auxiliary instrument may not be slid over the ramp or only with a destructive force. Furthermore, a ramp with a relatively low inclination may lead to the disadvantage that the auxiliary instrument end may not be deflected laterally enough.

SUMMARY OF THE INVENTION

The object of the invention lies in the solution of these problems. Furthermore there is to be put forward a hysteroscope which to a great extent may be disassembled for cleaning purposes and which has a favorable design of the respective fittings for the supply and removal of the rinsing fluid as well as for introducing the auxiliary instrument.

For achieving this object the hysteroscope according to the invention has a first ramp on which, sliding up, the distal end of the auxiliary instrument moved distally through the hysteroscope is deflectable in order with a further distal movement of the auxiliary instrument to bring its distal end region into a first position. There is also provided a deflection element with which the distal end region of the auxiliary instrument is deflectable into a second position beyond the first position, and specifically to a greater or lesser degree as required.

The first ramp may in principle be designed relatively-flat with a low gradient so that the distal auxiliary instrument end may be pushed easily over the ramp and deflected into its first position by bending, which may be considered as a supporting and preparatory measure for further deflection into a second position by pivoting out the deflection element, since this is possible without an excess force effort, after the distal end region of the auxiliary instrument has already been brought into an intermediate position by the ramp.

The deflection element designed as a pivotably mounted lever by way of a distal displacement out of a rest position, with a second ramp is pivoted against the distal end region of the auxiliary instrument in order to deflect this end region into the second position. With this the pivot bearing of the deflection element is usefully axially displaced with two parallel actuation rods which run through stationary guides which are attached at the outside on the inner shank and whose distal ends blend into a transverse web which runs through parallel slots into guides parallel to one another and likewise attached on the outside and on the inner shank, and which forms the pivot pin of the deflection element.

The ability of a hysteroscope of this or another type to be disassembled more easily amongst other things is achieved by designing the second fitting as a rinsing attachment, at the proximal end of the outer shank there is provided a coupling part with a cone, and the rinsing attachment may be placed from the proximal onto the cone, is displaceable proximally further onto the coupling part and is rotationally connectable to the coupling part in a manner lying against an abutment.

The rinsing attachment is equipped with a slotted clamping ring whose limbs on pushing onto the cone are elastically spread open and after the complete pushing of the rinsing attachment onto the coupling part under return deformation engage into an annular groove on the coupling part in order thus to fix the rinsing attachment by way of a positive fit connection. Furthermore on the coupling part there is provided a further annular groove which in cooperation with an annular housing part of the mounted rinsing attachment forms an annular channel which on the one hand is in connection with the channels of the rinsing attachment which lead the rinsing fluid and on the other hand via bores in the coupling part is in connection with a channel between the inner shank and the outer shank.

A useful connection of the two shanks results when in the coupling part there is provided a cone receiver into which from the proximal there may be pushed a coupling cone which is seated on the inner shank and which by way of latching elements is releasably connected to the coupling part.

Furthermore proximally to the coupling cone there may be a handle on whose proximal end there is provided a first fitting whose parts supplying the rinsing fluid via an obliquely proximally running channel are in connection with the channel forming the inner shank. Furthermore on the proximal end of the handle there may be provided a coupling with which optics insertable into and through the inner shank may be fastened on the inner shank.

The ability of a hysteroscope to be disassembled for cleaning purposes may furthermore be achieved by equipping the third fitting, on which the auxiliary instrument is introduced into and through the working channel of the hysteroscope, with a quick change valve which has a longitudinal channel for leading through the auxiliary instrument. This is partly inserted into a connection piece and by way of a bar may be fastened in the connection piece.

The quick change valve is on the distal side equipped with an elastic, centrally apertured sealing disk and proximally on its introduction connection piece projecting out of the connection piece is provided with a sealing cap which is placed provided centrally at the proximal end with an aperture through which the auxiliary instrument via the valve longitudinal channel further through the apertured sealing disk may be distally pushed into a working channel.

The fixing of the quick change valve in the connection piece may be effected such that the bar displaceable transversely to the longitudinal channel of the valve, in a locking position with two oppositely lying limbs on both sides engages with a positive fit into a groove on the quick change valve, and that by displacing the bar into a release position the positive fit is lifted and the quick change valve may be pulled from the connection piece.

BRIEF DESCRIPTION OF THE DRAWINGS

One embodiment example for a hysteroscope according to the invention is shown in the accompanying drawings and is described hereinafter. In the drawings there are shown in FIG. 1 the hysteroscope in a longitudinal section with an introduced auxiliary instrument.

DETAILED DESCRIPTION OF THE INVENTION

Figure 1:
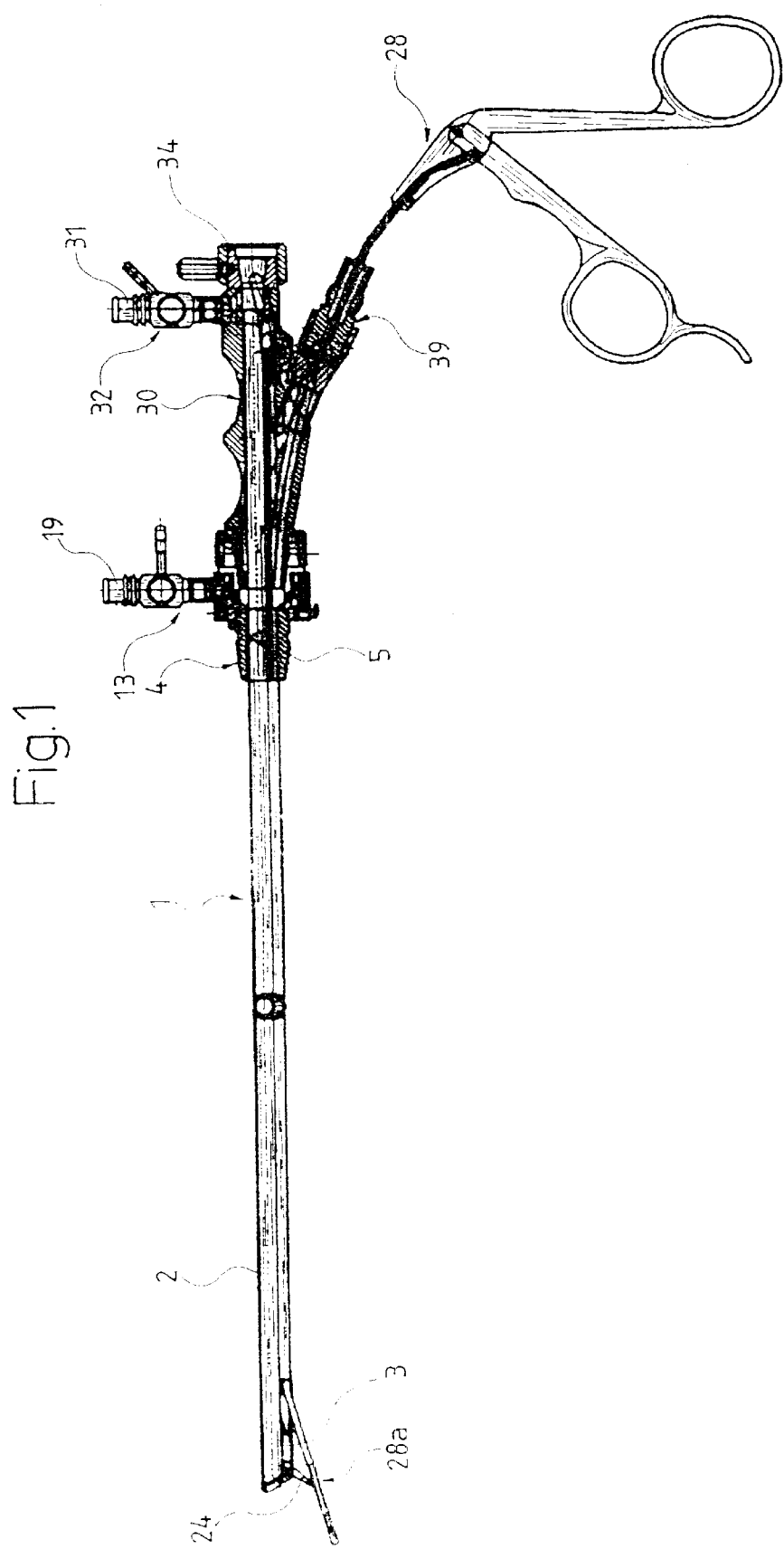

The hysteroscope 1 comprises an outer shank 2 which is formed ovally in cross section and which in the region of its distal end on the shank lower side is provided with a recess 3. Through this recess there may exit the distal end 28a of an auxiliary instrument 28 and this may he deflected at an angle to the instrument longitudinal axis, as This is shown in the FIGS. 1 and 2 and will be described later.

At the proximal end of the outer shank 2 there is located a coupling part 4 (FIG. 5b) which serves the releasable fastening of a rinsing attachment 13 (FIG. 5a) with a handle (not shown) and also the fastening of an inner shank 21. The releasable connection of the outer shank 2 to the rinsing attachment is effected via a recess in the coupling cone 5 of the coupling part 4, this recess forming an annular groove 6. A rinsing attachment 13 may be pushed onto the middle region of the coupling part 4 and rotatably movably fixed on this by way of a clamping ring 15 which according to FIG. 5c is slotted at the top.

In order to be able to slide the rinsing attachment 13 proximally onto the coupling part 4 the rinsing attachment is placed on the cone and pushed proximally. By way of the gradient of the cone the two limbs 15a and thus also the two ends of the clamping ring 15 are spread apart and laterally pivoted into an annular free space in the rinsing attachment, by which means the free inner diameter or passage of the clamping ring 15 is enlarged.

The rinsing attachment 13 may then further be pushed onto the coupling part 4 up to a diameter widening 4a of the coupling part 4, this extension being on the proximal side and forming an abutment. If the limbs 15a lie above the annular groove 6 the two ends of the clamping ring 15 and its limb 1 Sa return into their original position (FIG. 5c) and with this engage into the annular groove 6 of the coupling part 4. By way of pressure on a pin 16 the two ends of the clamping ring 15 which according to FIG. 5c are located above may be pressed against the conical end of a screw 17. With this the two limbs 15a are spread open and the engagement of the clamping ring 15 in the groove 6 is released so that the rinsing attachment 13 may be pulled from the coupling part 4.

By way of two O-rings 9 an annular groove 7 is sealed with respect to the annular housing part 14 of the rinsing attachment 13 so that rinsing fluid may be suctioned out of the body cavity via a tubing connection piece 19, a cock 18, the annular channel formed by the two parts 13 and 14 in the region of the annular groove 7 and via transverse bores 8 connecting this annular channel to a central channel in the outer shank 2.

FIG. 4 shows the inner shank 21 which may be inserted into the proximal end of outer shank 2 and which amongst other things serves for receiving endoscope optics O (FIG. 4a), for leading the auxiliary instrument 28, for receiving a device 22–26 deflecting the auxiliary instrument as well as for supplying rinsing fluid into the body cavity.

Figure 2:
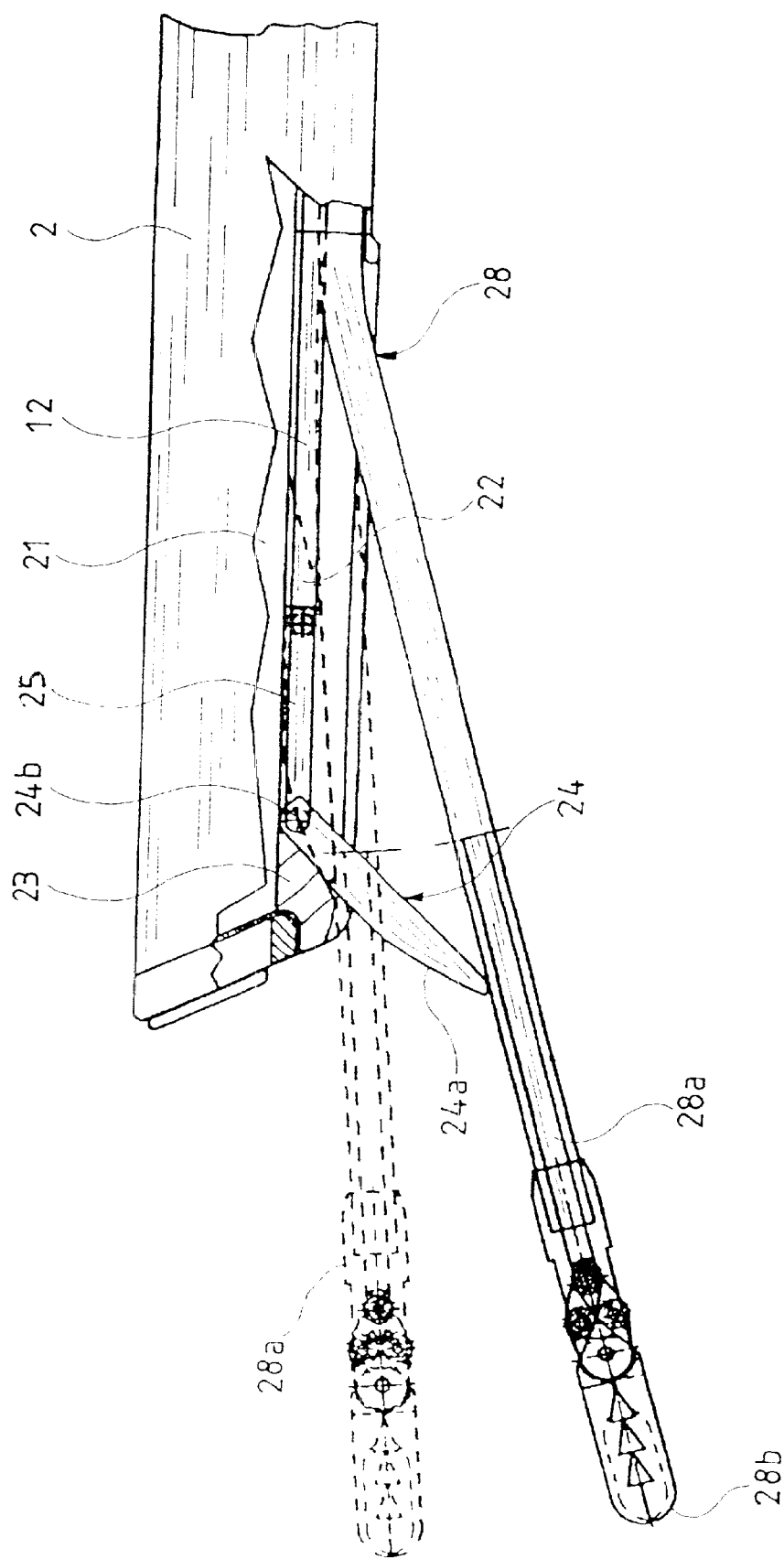
FIG. 2 the distal end region of the hysteroscope according to FIG. 1 in an enlarged scale, FIG. 3 the proximal end region of the hysteroscope according to FIG. 1 in an enlarged scale, FIG. 4 the inner shank of the hysteroscope seen from below with a means for displacing the deflection element, FIG. 4a a section through the inner shank in the region of the deflection element, FIG. 4b a lateral view of the embodiment form shown in FIG. 4a with an inner shank shown only partly, FIG. 5a a rinsing attachment for removing rinsing fluid, FIG. 5b the proximal end region of the outer shank in section, FIG. 5c the rinsing attachment according to FIG. 5a with part sections, FIG. 6 a quick change valve for introducing auxiliary instruments, in a longitudinal section and FIG. 6a a cross section through the quick change valve according to FIG. 6 in the region of the slider.

The device for deflecting the distal end 28a of the auxiliary instrument 28 is also shown in FIG. 2. This shows two ramps arranged at an axial distance to one another, specifically a first ramp 22 and a second ramp 23, as well as a deflection element 24 in the form of a lever whose length determines the minimum distance between the two ramps, since in a rest position it lies between the ramps directed essentially parallel to the axis. On introducing the endoscope 1 into the body cavity the element 24 should remain in a position parallel to the instrument longitudinal axis and should not protrude outwards through the recess 3. As is evident from FIG. 2 the deflection element 24 has an oblique run-up surface 24a which initially with the pivoting-out of the deflection element 24 lies and slides on the oblique surface of the ramp 23.

For the axial displacement of the deflection element 24 there are two parallel actuation rods 25 which are arranged and guided below the inner shank 21. For bending the distal end region 28a of the semi-rigid auxiliary instrument 28 relatively large forces are required which is why the actuation rods 25 and also the deflection element 24 as well as its mounting are designed to be stable. In this context the guide sleeves 2.7 which are axially passed through by the actuation rods and are rigidly fixed below the inner shank 21 are also important. The distal ends of the actuation rods 25 blend into a transverse web 25a which runs through the deflection element 24 and forms its pivot pin 24b.

The auxiliary instrument is introduced via a valve 39 and with its distal end 28b first comes to bear with the ramp 22 so that the auxiliary instrument end with a further distal movement of the auxiliary instrument slides on the ramp 22 and finally assumes the first position shown dashed in FIG. 2. For the case that the auxiliary instrument end is to be deflected even further laterally into a second position, this is effected by pivoting out the deflection element 24 from the rest position.

This is effected in that the deflection element 24 sliding up on the second ramp 23 by way of the actuation rods 25 is displaced distally with the simultaneous pivoting from the original position parallel to the axis. By way of guides 26 arranged longitudinally on both sides of the ramps 22, 23, fastened below on the inner shank 21 and equipped with longitudinal slots, it is ensured that the transverse web 25a engaging through the longitudinal slots and thus the rotation point or pivot pin 24b of the deflection element 24 may not change with respect to the distance to the inner shank 21. By way of this the distal displacement of the deflection element 24 in cooperation with the ramp 23 effects the pivoting-out of the deflection element and a further continuous deflection end and the deflection element have assumed e.g. a working position shown in FIG. 2.

With the proximal displacement of the actuation rods 25 the deflection element 24 under the pressure of the auxiliary instrument 28 which attempts to return back into its original straight form, is pressed back from the working position into the rest position. With this the rear side of the deflection element 24 slides on the lower side of the inner shank 21. The rest position is reached when the deflection element 24 assumes the position shown in FIG. 4b and lies directed essentially parallel to the inner shank 21, wherein the surface 24a bears against the oblique surface of the ramp 23.

As one may deduce from FIGS. 1 and 3 the releasable connection between the inner shank 21 and the outer shank 2 is effected in a known manner with a cone receiver 10 arranged at the proximal end of the outer shank 2 in the coupling part 4 and with a coupling cone 29 arranged on the inner shank 21. With the help of a rotational lock 11 latching balls or latching elements 12 are movable into corresponding recesses in the coupling cone 29, in order thus to releasably connect the two shanks 2, 21 to one another.

To the coupling cone 29 there proximally connects a handle 30 which at its proximal-side end is provided with a fitting 32 for the supply of rinsing fluid as well as with a coupling 34 having a cone receiver, for the releasable connection of the optics 0 to be introduced into the inner shank 21.

As one may deduce from FIG. 3, a channel 33 connecting the tubing connection 31 and the cock 32a of the fitting 32 and the central channel in the inner, shank 21 is located directly at the proximal end of the inner shank, and specifically running inclined in the direction towards the proximal end, so that this region is very, easily accessible and therefore may be cleaned to the desired extent.

On the underside of the handle 30 there is provided a receiving bore 37 which runs obliquely to the instrument longitudinal axis and in which the cylindrically formed end of the connection piece 36 receiving a quick change valve 36 is unreleasably fastened for introducing the auxiliary instrument 28. For guiding the auxiliary instrument, proceeding from the connection piece 36 there is provided a slightly arcuately running channel 38 which is formed by a tube and which opens into the free space or longitudinal channel 1.2 remaining between the inner shank 21 and the outer shank 2.

Referring to FIG. 6, the quick change valve 39 inserted into the proximal end of the connection piece 36 consists of metal or elastic material and comprises on the distal side a centrally apertured elastic sealing disk 40 and proximally a sealing cap 41 which is placed on the introduction connection piece 39a of the valve and which is provided centrally with an aperture. The releasable connection between the connection piece 36 and the quick change valve 39 is effected with a bar 42 which is displaceable transverse to the valve longitudinal axis 39b, according to FIG. 6a has a rectangular shape, is manufactured of a round material, for example spring wire, and with oppositely lying limbs 42a on both sides engages into a groove 39c on the circumference of the quick change valve 39 and secures this against the pulling out of the connection piece 36 by way of the thus created positive fit connection. If the bar is displaced out of the locking position according to FIG. 6a upwards into a release position, the positive fit connection on account of recesses 42b on the inner sides of the bar limb 42a is lifted, so that the valve 39 may be removed.

The bar limbs 42a are usefully guided vertically in bores of the connection piece 36 which in pairs lie opposite one another.

On inserting the bar 42 into the annular groove 39c the quick change valve 39 is pressed in the direction of the connection piece 36 and, as long as it consists of elastic material is slightly deformed in the connection piece. If the bar 42 has finally reached the blocking position shown in FIG. 6a the quick change valve may again be relaxed somewhat proximally since the bar limbs 22b in the region of their connection to the quick change valve 39 are weakened and sunk in by way of material recesses.

The respective cock 18, 32a for the tubing connections or tubing connection pieces 19, 31 are equipped with levers 20, 32b with which the cock plugs may be rotated by hand and the cocks may be opened and closed. Furthermore on the handle 30 there is pivotably arranged a lever 43 with which the deflection element 24 via the actuation rods 25 may be displaced from the rest position into the working position according to FIG. 2 and again back into the rest position.

What is claimed is:

1. A hysteroscope for carrying out endoscopic operations in the uterus by way of an elastically laterally deflectable auxiliary instrument having a distal end, said hysteroscope comprising an inner shank and an outer shank surrounding the inner shank and forming a longitudinal channel between said inner shank and said outer shank, a first fitting for supplying rinsing fluid to be led through the inner shank into the uterus, a second fitting for removing rinsing fluid from the uterus via the longitudinal channel, a third fitting at which the auxiliary instrument is introducible into the hysteroscope and is further axially movable through a working channel, a first ramp on which the distal end of the auxiliary instrument moved axially through the hysteroscope is laterally deflectable, in order with an axial movement of the auxiliary instrument against said first ramp to deflect said distal end laterally in a direction into a first position, a second ramp which is not movable with respect to said inner shank, said second ramp being situated axially beyond said first ramp, and a deflection element with which the distal end of the auxiliary instrument is further laterally deflectable in said direction away from the first ramp and into a second position beyond the first position, wherein the deflection element is a pivotably mounted lever which is pivotable about a pivot bearing out of a rest position in response to axial displacement of said lever against said second ramp so that the lever bears against the auxiliary instrument in order to deflect the distal end further in said direction into the second position.

2. A hysteroscope according to claim 1 wherein the pivot bearing of the deflection element is axially movable by two parallel actuation rods which run through stationary guide sleeves attached on the outside on the inner shank.

3. A hysteroscope according to claim 2, wherein the actuation rods have distal ends which blend into a transverse web which runs through longitudinal slots in guides parallel to one another and attached on the outside on the inner shank, which web forms the pivot bearing.

4. A hysteroscope according to claim 1 wherein the outer shank has a proximal end provided with a coupling part with a coupling cone and wherein the second fitting can be placed onto the coupling cone, is displaceable proximally further onto the coupling part, and lying against an abutment is connectable to the coupling part in a rotatably movable manner.

5. A hysteroscope according to claim 4, wherein the second fitting comprises a slotted clamping ring having limbs which on pushing onto the cone may be elastically spread open and after pushing the second fitting onto the coupling part under return deformation engage an annular groove on the coupling part.

6. A hysteroscope according to claim 4, wherein the coupling comprises an annular groove which in cooperation with an annular housing part of the assembled rinsing attachment forms an annular channel which channels, of the rinsing attachment, supplying the rinsing fluid, via bores in the coupling part to a channel between the inner shank and the outer shank.

7. A hysteroscope according to claim 4, wherein in the coupling part comprises a cone receiver into which from the proximal end there may be pushed a coupling cone seated on the inner shank, said coupling cone being releasably connectable to the coupling part by way of latching elements.

8. A hysteroscope according to claim 7, wherein to the coupling cone there proximally connects a handle on whose proximal end there is provided the first fitting, the first fitting supplying the rinsing fluid via an obliquely proximally running channel connected to a channel formed by the inner shank.

9. A hysteroscope according to claim 8, wherein the proximal end of the handle comprises a coupling with which optics insertable into and through the instrument shank may be fixed.

10. A hysteroscope according to claim 1 wherein the third fitting comprises a connection piece and a quick change valve which has a longitudinal channel for leading through the auxiliary instrument, said quick change valve being inserted into the connection piece and by way of a bar can be fixed in the connection piece.

11. A hysteroscope according to claim 10, wherein the quick change valve comprises a distal end having an elastic, centrally apertured sealing disk a proximal end having an introduction connection piece, and a sealing cap which is placed onto this introduction connection piece and which centrally on the proximal end is provided with a aperture.

12. A hysteroscope according to claim 10, wherein the bar in a locking position with two opposite limbs on both sides engages with a positive fit into a circumferential groove on the quick change valve and wherein by displacing the bar transversely to the longitudinal axis of the quick change valve into a release position the positive fit is lifted and the quick change valve may be pulled out of the connection piece.

13. A hysteroscope for carrying out endoscopic operations in a uterus by way of an elastically deflectable auxiliary instrument having a distal end, said hysteroscope comprising:

an inner shank defining an axially extending working channel through which an auxiliary instrument can be moved axially;

a first ramp which is not movable with respect to said inner shank, said first ramp being arranged to deflect said distal end of said auxiliary instrument in a direction laterally of said working channel when said auxiliary instrument is moved axially against said first ramp;

a second ramp which is not movable with respect to said inner shank, said second ramp being situated axially beyond said first ramp; and a lever which is movable axially against said second ramp and is pivotable to deflect said distal end of said auxiliary instrument laterally further in said direction when said lever is moved axially against said second ramp.

14. A hysteroscope as in claim 13 further comprising at least one actuation rod and means for guiding said actuation rod parallel to said working channel, said lever being pivotably mounted to said at least one actuation rod.

15. A hysteroscope as in claim 14 comprising a pair of said actuation rods, said means for guiding said at least one actuation rod comprising a pair of guide sleeves fixed to said inner shank and carrying respective said actuation rods, said lever being mounted on a pivot pin between said rods.

* * * * *